| United States Patent [19] | [11] Patent Number: 4,801,741 |
| Guglielmo et al. | [45] Date of Patent: Jan. 31, 1989 |

[54] PROCESS FOR THE PREPARATION OF PERHALOHYDROCARBON HYPOCHLORITES

[75] Inventors: Giorgio Guglielmo, Mirano; Guglielmo Gregorio, Milan; Pierangelo Calini, Rho, all of Italy

[73] Assignee: Ausimont S.p.A., Milan, Italy

[21] Appl. No.: 93,040

[22] Filed: Sep. 4, 1987

[30] Foreign Application Priority Data

Sep. 8, 1986 [IT] Italy .............................. 21631 A/86

[51] Int. Cl.$^4$ ............................................. C07C 71/00
[52] U.S. Cl. .................................................... 560/300
[58] Field of Search ..................... 560/300; 260/543 F

[56] References Cited

U.S. PATENT DOCUMENTS 3,769,312 10/1973 Gould et al. ...................... 560/300
3,842,156 10/1974 Young et al. ...................... 560/300

OTHER PUBLICATIONS

D. E. Gould, JACS/91:6/Mar. 12, 1969, pp. 1310–1313.
Young, CA 77(1) 4893f, 1972.
Young D., CA 73(25) 130581h, 1970.

*Primary Examiner*—Paul J. Killos
*Attorney, Agent, or Firm*—Stevens, Davis, Miller & Mosher

[57] ABSTRACT

Process for the preparation of chloro-oxy-halo-compounds by means of the direct reaction between FCl and organic compounds having a molecular structure wherein an oxygen atom is directly linked to a carbon atom in the carbonyl form, in the presence of a catalyst constituted by an alkali metal or alkali-earth metal fluoride, preferably selected from K, Rb, Cs, Ba, Sr, the reaction being carried out in the gas phase and in continuous.

8 Claims, No Drawings

PROCESS FOR THE PREPARATION OF PERHALOHYDROCARBON HYPOCHLORITES

FIELD OF THE INVENTION

The present invention relates to a process for the preparation of chloro-oxy-halo-compounds. More particularly, the present invention relates to a continuous process for the preparation of chloro-oxy-halo-compounds having the general formula:

$$(R)_nC(F)_m\text{---}OCl \qquad (1)$$

wherein R is an alkyl, cycloalkyl, aromatic, heterocyclic, polyether radical, containing from 1 to 12 carbon atoms, preferably from 1 to 6 carbon atoms, fully halogenated with fluorine and/or bromine, chlorine; n is 0, 1 or 2; m is 3−n. If n=2, R can represent radicals equal to or different from each other.

BACKGROUND OF THE INVENTION

The preparation of chloro-oxy-derivatives of perfluoroalkanes results known from the technical and patent literature: however, the described processes are mostly unsatisfactory, as is better explained hereunder.

Schack and Naya in J.A.C.S. (1969) 2902-91, 11 describe the preparation, by a batch process, at temperatures ranging from −78° C. to room temperature for the first term of the series, $CF_3OCl$, whilst, for the higher terms, it operates at −78° C. The operation is carried out with the reactants being in the liquid phase, possibly under their autogenous pressure. It is stated that for the higher terms, the low temperature adopted in the reaction is due to their high instability at room temperature. As relates to the first term, it would result that even at room temperature, the formation rate is not very high (only 60% after 1 hour).

U.S. Pat. No. 3,842,156 claims gaseous catalysts of the type of $SbF_5$, HCl, $BF_3$, which would be preferable to the metal fluorides of the prior art, and would be furthermore suitable for the gas-phase reaction. Actually, the preparation described are carried out at −20° C. on reactants in the liquid state, with very long reaction times (24 hours).

U.S. Pat. No. 3,769,312: in this case too, the process is of batch type, carried out at a low temperature of from −78° to 0° C., preferably −20° C., with reaction times of the order of 10 hours.

Finally, the French Pat. No. 1,589,946 relates exclusively to the synthesis of $CF_3OCl$, carried out in the gas phase, at room temperature, batchwise: reaction times of some hours are mentioned. This patent uses catalysts prepared in a special way from $MgF_2$ and fluorinated $Al_2O_3$.

We can conclude hence that from the prior art examined, it results in general that the reaction is carried out in the *liquid phase*, with very long reaction times. The preferred temperatures are lower than, or at maximum equal to 0° C., preferably −78° C. or −20° C. According to Schack, at room temperature, for the first term, the yield is of 60% only after 1 hour, and for reaching a 99% yield, approximately 12 hours are necessary.

The only process in the gas phase is the one disclosed by the French Pat. No. 1,589,946, limitedly to the synthesis of $CF_3OCl$, always by a batch process. In this case too, the times mentioned are very long.

THE PRESENT INVENTION

A purpose of the present invention is to provide an improved process for preparing the chloro-oxy-compounds, which does not show the limitation and the drawbacks of the processes of the prior art.

More particularly, a purpose of the present invention is to provide a continuous industrial process for the preparation of the chloro-oxy-compounds.

A further purpose of the present invention is to provide an industrial process which makes it possible to produce, in a selective way, and with high yields, the desired chloro-oxy-compound.

Still a further purpose of the present invention is to provide an industrial process which makes it possible to produce chloro-oxy-compounds with a high productivity and at a high purity level, without the need for a subsequent isolation and/or processing, so to prevent the risks and the limitations connected with their high unstability.

The applicant has now surprisingly found, and it is the object of the present invention, that these and other purposes are achieved by carrying out the direct reaction, in continuous mode, in the gas phase, between FCl and organic compounds, having a molecular structure wherein an oxygen atom is directly bonded to a carbon atom in carbonyl form, in the presence of a solid catalyst constituted by a fluoride of alkali metal or alkali-earth metal, preferably selected from K, Rb, Cs and Ba, Sr, in particular CsF, preferably supported on or mixed with a metal in particular copper. Such catalyst, in the process of the invention, shows a rather high life of the catalytic activity, of the order of some hours.

The reaction temperature is maintained at values comprised within the range of from 0° to +100° C., preferably of from 25° to 50° C. The reaction times are always shorter than 10 minutes, and, in particular, shorter than 1 minute.

In as much as it was found that by operating under the above shown operating conditions, with particularly active catalysts, the reaction takes place with quantitative yields within very short times, of the order of seconds, it is suitable, for accomplishing a reliable control, to dilute the reactants with an inert gas. This latter can be, e.g., nitrogen, a chlorofluorocarbon inert under the reaction conditions, in particular $C_2F_4Cl_2$, or He.

The reaction can be run at a pressure equal to or higher than atmospheric pressure.

The above-indicated catalyst is used at a granulometry of from 50 to 1000, preferably comprised within the range of from 250 to 500 microns, and it can be obtained by grinding. The catalyst is preferably mixed with metal particles of dimensions of the order of some mm. The metal can be, e.g., Cu, Ni or Al. In particular the catalyst is supported by the metal particles.

The reactants used must be free from $H_2O$ and HF, and $H_2$ and hydrogenated compounds, e.g., alcohols, aldehydes, hydrocarbons, must not be present.

As already said, the chloro-oxy-halo-compounds which are the object of the present invention can be directly used, it being not necessary that they are isolated and purified for the subsequent uses, and, in particular, for the reaction with olefins; for obtaining then, by dehalogenation, fluoroalkyl-vinylethers, not easily available compounds which are used for preparing modified fluorinated polymers, plastomers and fluoroelastomers.

It is well known that, to date, the possibility of preparing these latter compound on an industrial scale by this route was limited by the excessive cost of preparation of the fluoroalkyl-chloro-oxy-compounds.

According to the prior art, in fact, such compounds have always been prepared heretofore by batch processes, with very small amounts of reactants, of the order of millimoles.

The starting compounds used in the present invention contain a carbonyl group, and have the general formula:

(II)

wherein:

R' can be F or perfluoroalkyl;

R=F or a fluorinated hydrocarbon radical which can contain also other halogens of the type as defined in formula (I).

In particular, the starting products are those wherein R' is F and R is F or a $C_1$-$C_6$ perfluoroalkyl, such as: $COF_2$, $CF_3COF$, $C_2F_5COF$, $C_3F_6COF$, $CF_2BrCOF$.

In particular, for obtaining $CF_3OCl$, the starting product $COF_2$ can be advantageously obtained according to the continuous process disclosed as the 1st step in Italian patent application No. 21,172 A/86, to the same applicant, by reaction between CO and $F_2$, by directly using the gaseous reaction mixture from the 1st step in the subsequent reaction with FCl.

The reactants are supplied in continuous, in the gas phase, preferably under a slight pressure and in equimolar amounts, with flowrates of each reactant higher than $5.10^{-6}$ mol/h per catalyst gram. Flowrates of each reactant comprised within the range of from $10^{-4}$ to $10^{-1}$ mol/h per catalyst gram are preferred.

In general, the reactor is of stainless steel or of copper and its alloys, or of other materials inert towards the reactants.

A particular advantage offered by the present invention consists in that the chloro-oxy-compound obtained by means of the process of the invention can be used as such as a gaseous mixture with the possible diluent, in the reaction with halogenated olefins for obtaining the corresponding ethers.

For a better understanding of the possibilities of practical embodiment of the present invention the following illustrative, non-limitative examples are given.

In all the examples, as the reactant FCl was used, which was obtained in the following way: to a nickel reactor of 1 liter of capacity, 3 l/h of chlorine and 3.1 l/h of fluorine are delivered, with the reactor being maintained at the temperature of 400° C. At the reactor outlet, a cold trap, kept cooled at −80° C., secures the removal of $ClF_3$ and the obtained gas is FCl, at a good purity level; it is used as such as the reactant in the hereunder reported examples.

EXAMPLE 1

A cylindrical steel reactor of 50 $cm^3$ of capacity is packed with copper wire fraggments, on which cesium fluoride was deposited by evaporation from a methanol solution. The amount of CsF in the so-prepared reactor is 15 g. The reactor is maintained at 30° C. by means of a temperature-controlled bath. To the reactor, a gas mixture of 6 l/h of chlorine fluoride (FCl), prepared according to the above-reported process and 5 l/h of trifluoriacetyl fluoride is fed. This latter reactant is in a slightly lower amount relatively to the stoichiometric, for the purpose of securing the complete conversion thereof. As the diluent, helium is used in an amount of 30 l/hour. The reaction mixture is analysed by I.R. spectrophotometry and gas-chromatography. Detected is: the presence of FCl, used in a slight excess, the sesappearance of

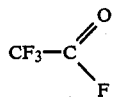

and the presence of one single product detectable by chromatography, and corresponding to the derivative $CF_3CF_2$—OCl. The I.R. spectrum of the gas corresponds to that reported on J.A.C.S. 91 2902 (1969).

By flowing the so obtained gas for a 2-hour time directly through a glass reactor kept cooled at −80° C., containing $CF_2Cl$—$CF_2Cl$, acting as the reaction solvent, and at the same time feeding $CFCl=CFCl$ in an equimolar amount with the trifluoroacetyl fluoride supplied to the hypochlorite synthesis reactor, at the end of the reaction a solution is obtained wherein the main product, obtained with a yield of about 70% by mol relatively to the olefin fed, is

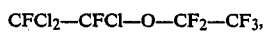

$CFCl_2$—$CFCl$—O—$CF_2$—$CF_3$, identified by N.M.R. analysis, and which can be isolated by distillation. Other reaction byproducts are lower boiling and are distilled off as overhead products.

EXAMPLE 2

Through the same reactor of Example 1 a mixture is flown of FCl (6 l/h) and 6 l/h of $COF_2$ diluted in 30 l/h of helium, obtained by mixing inside an externally water-cooled tube, CO, $F_2$, helium, respectively in the amounts of respectively 3+3+30 l/h.

In this case, the reactor is maintained at 50° C. In the outlet reaction product the conversion is nearly total, and the I.R. spectrum of the gas shows two bands at 730 and 790 $cm^{-1}$ which in the technical literature are attributed to the presence of the OCl group of $CF_3OCl$.

EXAMPLE 3

Through the same reactor of Example 1, a mixture is flown of FCl (6 l/h) and $CF_2Br$—COF (4 l/h) diluted with 30 l/h of helium. The reactor is maintained at 20° C.

On the stream leaving the reactor it is observed that $CF_2Br$—COF has reacted by more than 90%, as it is demonstrated by the nearly disappeared I.R. adsorption of C=O group and by the presence of the two new absorption bands at 775 and 1290 $cm^{-1}$ attributed, by analogy with the previous cases, to the compound

$CF_2Br$—$CF_2OCl$.

What we claim is:

1. Process for the preparation of chloro-halo-compounds having the formula:

$(R)_nC(F)_m$—OCl   (1)

wherein R is an alkyl, cycloalkyl, aromatic, heterocyclic, polyether radical, containing from 1 to 12 carbon atoms, fully halogenated with bromine, chlorine and/or fluorine; n is an integer comprised within the range of from 0 to 2; m is an integer equal to 3−n, and wherein, if n=2, R represents radicals equal to or different from each other, by means of the direct reaction in the presence of a solid catalyst constituted by a fluoride of an alkali metal or of an alkali-earth metal, between FCl and organic compounds, having a molecular structure wherein an oxygen atom is directly bonded to a carbon atom in carbonyl form, characterized in that the reaction is carried out in the gas phase at a temperature comprised within the range of from 0° to 100° C., under conditions of continuous feeding of the reactants and of removal of the reaction product, so that the stay time of the reactants inside the reaction medium is shorter than 10 minutes, and under conditions of removal of the reaction heat for maintaining the temperature at a not higher value than pre-established.

2. Process according to claim 1, characterized in that the organic compounds, having a molecular structure wherein an oxygen atom is directly bonded to a carbon atom in the carbonyl form, have the formula:

wherein: R' can be F or perfluoroalkyl, R=F or a fluorinated hydrocarbon radical which can contain also chlorine and/or bromine.

3. Process according to claim 2, characterized in that R represents a perfluoroalkyl radical containing from 1 to 6 carbon atoms.

4. Process according to any of preceding claims, characterized in that the reaction between FCl and organic compounds having a molecular structure in which an oxygen atom is directly bonded to a carbon atom in the carbonyl form, is carried out by means of the continuous flowing of the reactants in the gas phase through a fixed bed containing the catalyst, and capable of securing the desired heat exchange.

5. Process according to any of preceding claims, characterized in that it is carried out in the presence of a metal material essentially inert towards fluorine, used as a support for the catalyst.

6. Process according to claim 4 or 5, characterized in that the catalyst is admixed with the metal material as shavings, Rasching rings and similar packing bodies.

7. Process according to claim 5 or 6, characterized in that the metal material is copper or its alloys.

8. Process according to any of preceding claims, characterized in that the reactants are fed in diluted form with an inert gas, at concentrations comprised within the range of from 5 to 70% by volume.

* * * * *